US006632585B1

(12) United States Patent
Nakamura

(10) Patent No.: US 6,632,585 B1
(45) Date of Patent: Oct. 14, 2003

(54) PHOTOSENSITIVE COMPOSITION, AND OPTICAL WAVEGUIDE ELEMENT AND PROCESS FOR PRODUCING THE SAME

(75) Inventor: Koichiro Nakamura, Osaka (JP)

(73) Assignee: Nippon Sheet Glass Co., Ltd., Osaka (JP)

(*) Notice: Subject to any disclaimer, the term of this patent is extended or adjusted under 35 U.S.C. 154(b) by 96 days.

(21) Appl. No.: 09/889,095

(22) PCT Filed: Nov. 10, 2000

(86) PCT No.: PCT/JP00/07949

§ 371 (c)(1), (2), (4) Date: Jul. 11, 2001

(87) PCT Pub. No.: WO01/37049

PCT Pub. Date: May 25, 2001

(30) Foreign Application Priority Data

Nov. 12, 1999 (JP) ............................. 11-323005

(51) Int. Cl.$^7$ ..................... G03C 1/73; G03F 7/027; G03F 7/20; G03F 7/30; G03F 7/40
(52) U.S. Cl. ................ 430/281.1; 430/285.1; 430/321; 430/325; 430/330; 430/328; 522/84; 522/85; 522/86
(58) Field of Search ............................. 522/84, 85, 86; 430/281.1, 287.1, 285.1, 330, 325, 321, 328; 556/437, 440, 442, 465, 482, 484

(56) References Cited

FOREIGN PATENT DOCUMENTS

| EP | 549228 | 12/1992 |
|----|--------|---------|
| JP | 7-331173 | 12/1995 |
| JP | 8-313742 | 11/1996 |
| JP | 8-327842 | 12/1996 |
| JP | 10-148729 | 6/1998 |
| JP | 10-253845 | 9/1998 |
| JP | 11-202102 | * 7/1999 |
| JP | 2000-180643 | 6/2000 |
| JP | 2000-248114 | * 9/2000 |
| WO | 98/25862 | 6/1998 |

OTHER PUBLICATIONS

Mino et al, *Fabrication of self–assembled Monolayer Patterns by Selective Electron Beam Irradiation and a Chemical Adsorption Technique*, Thin Solid Films, vol. 243 p. 374–377, 1994.*

Chemical Abstract for JP 11–202102. (Tomokazu et al), Jul. 30, 1999.*
Machine–assisted English translation for JP 11–202102 (provided by Japan Patent office), Jul. 30, 1999.*
Machine assisted English translation for JP 2000–248114 (provided by Japan Patent office), Sep. 12, 2000.*
S. Najafi et al., "Sol–Gel Glass Waveguide and Grating on Silicon", Journal of Lightwave Technology, vol. 16, No. 9, Sep. 1998, pp. 1640–1646.
T. Touam et al., "Theoretical and Experimental Study of Ridge Waveguides with Bragg Grating Derived form Hybrid Sol–Gel Glasses", SPIE, vol. 3282, pp. 17–30.
M.P. Andrews et al., "Collateral Densification Associated with the Photoresponse of Hybrld Sol–Gel Glasses for Depositing Bragg Gratings on Ridge Waveguides", SPIE, vol. 3282, pp. 50–58.
Optonews, No. 2, pp. 31–32, 1999, with partial English translation.
M. Mennig et al., "A Novel Non–Hydrolytic Sol–Gel Route to Low OH– and CH–containing Organic–Inorganic Composites", SPIE, vol. 3469, pp. 68–78, 1998.

* cited by examiner

*Primary Examiner*—Janet Baxter
*Assistant Examiner*—Sin J. Lee
(74) *Attorney, Agent, or Firm*—Wenderoth, Lind & Ponack, L.L.P.

(57) ABSTRACT

To provide a light transmitting material which has high transmission at wavelength ranges used for communication and excellent characteristic properties such as heat resistance, water resistance and chemical resistance, and makes it possible to produce a grating and incorporate it in a mounting module with ease. A photosensitive composition for forming a light transmitting material comprising a silane compound or hydrolysis/dehydration condensation reaction product thereof, a photoinitiator and water, the silane compound being represented by the following formula (1):

$$R^1SiX^1_3 \qquad (1)$$

wherein $R^1$ is an organic group having a polymerizable carbon-carbon double bond, and $X^1$ is a hydrolyzable group or atom, with the proviso that at least 40% of the total number of hydrogen atoms of the organic group $R^1$ are substituted by at least one substituent atom selected from the group consisting of deuterium, fluorine, chlorine and bromine.

22 Claims, No Drawings

PHOTOSENSITIVE COMPOSITION, AND OPTICAL WAVEGUIDE ELEMENT AND PROCESS FOR PRODUCING THE SAME

This application is a 371 of PCT/JP00/07949 filed Nov. 10, 2000.

FIELD OF THE INVENTION

The present invention relates to a photosensitive composition, an optical waveguide element comprising the same and a process for producing the optical waveguide element.

PRIOR ART

Along with the rapid spread of the Internet and multimedia, a need for optical communication systems having higher speed and larger capacity has recently been growing. As a means of meeting the need, much attention is being paid to a wavelength multiplex communication system (WDM) which eliminates the need of increasing the number of optical fibers and makes use of the existing optical fibers. Optical parts and materials are necessary for the construction of this system. Among the optical parts are an optical waveguide element, an optical filter element and the like. For these optical parts and materials for optical communication, the supply of a material which needs to have transmission at communication wavelength ranges and such characteristic properties as heat resistance, water resistance and chemical resistance, and makes it possible to produce them and incorporate them in a mounting module with ease is desired.

The following materials (i) to (vi) are known as the material which satisfies the above requirements:

(i) a coating solution composition for forming an optical material which comprises a trifunctional silane and metal alkoxide, and an optical material formed therefrom (JP-A 7-331173) (the term "JP-A" as used herein means an "unexamined published Japanese patent application"), (ii) a resin material for optical transmission lines which is a partial hydrolysis and condensation polysiloxane resin of deuterated tetraalkoxysilane and an optical waveguide formed therefrom (JP-A 8-313742), (iii) an optical waveguide element having a grating manufactured from a photosensitive material comprising methacryloxypropyl trimethoxysilane, zirconium alkoxide and acrylic acid (JOURNAL OF LIGHTWAVE TECHNOLOGY, Vol. 16, No. 9, pp. 1640–1646, September 1998, SPIE Vol. 3282, pp. 17–30 and SPIE Vol. 3282, pp. 50–58)

(iv) a polymer optical waveguide element having a low loss at a communication wavelength (Optonews, No. 2, pp. 31–32, 1999), (v) an organic-inorganic hybrid material having excellent transparency and comprising methacryloxypropylmethyl dichlorosilane (MPMDCS), 1H, 1H, 2H, 2H-tridecafluorooctylmethyl dichlorosilane (FOMDCS) and heptadecafluorodecyl methacrylate (HFDMA) (M. Menning, M. Zahnhausen, H. Schmidt, Proc. SPIE Vol. 3469, pp. 68–78, 1998) (The C—H group of MPMDCS which is a photosensitive raw material remains unchanged and FOMDCS having a large number of C—F groups and HFDMA which is a photosensitive organic monomer are added excessively to reduce the number of the C—H groups), and (vi) an organic-inorganic hybrid material which comprises tetraalkoxysilane, alkyltrialkoxysilane and aryltrialkoxysilane (WO 98/25862) (This publication shows that the absorption of IR having a wavelength of 1.3 $\mu$m and a wavelength of 1.553 $\mu$m derived from the C—H bond can be reduced by using $CD_3Si(OC_2H_5)_3$ and $C_6D_5Si(OC_2H_5)_3$).

However, the above prior arts have the following problems. First, since the above material (i) has an alkyl group and alkoxy group and its absorbed harmonic component based on the C—H bond is at a near infrared range, it cannot be said that it has high transmission at communication ranges of 1.55 $\mu$m and 1.3 $\mu$m.

The material (ii) has such a problem that when a film having a thickness required for the formation of an optical waveguide element is to be formed therefrom, the film is easily cracked although the loss of light having communication wavelengths is reduced by using deuterated tetraalkoxysilane. Further, it is not easy to form a diffraction grating on the optical waveguide.

Since the element (iii) is made from a photosensitive material, an optical waveguide having a grating can be easily manufactured by a method such as optical processing. However, like the above material (i), it cannot be said that the element has high transmission at communication ranges. As the element (iv) is made from a polymer, it does not always have satisfactory workability, reliability for parts and stability.

The above organic-inorganic hybrid material (v) must contain an organic component having a C—F group in excess to ensure light transmission and only an organic-inorganic hybrid material having an extremely small content of an inorganic component is provided. The content of the inorganic component cannot be increased in full so as to improve thermal characteristics (environmental resistance and dimensional stability obtained by reducing thermal expansion coefficient).

The above material (vi) cannot be used as a material to be processed by photolithography for the manufacture of a diffraction grating by double-beam interference exposure, the manufacture of an optical waveguide by exposure using a photomask and patterning by the leaching of an unexposed portion, or the manufacture of a diffraction grating by phase mask exposure because the alkyl group (methyl group) or aryl group (phenyl group) contained in $CD_3Si(OC_2H_5)_3$ and $C_6D_5Si(OC_2H_5)_3$ does not have photopolymerizability or thermopolymerizability.

SUMMARY OF THE INVENTION

The present invention has been made in view of the above problems of the prior art. That is, it is an object of the present invention to provide a photosensitive composition which has high transmission at wavelength ranges used for communication, excellent characteristic properties such as heat resistance, water resistance and chemical resistance and is used as a process material which makes it possible to form a grating and incorporate it in a mounting module with ease. It is another object of the present invention to provide a photosensitive composition for forming a light transmitting material which enables the free control of the proportions of an organic component and an inorganic component and fine light processing through exposure and has a photosensitive organic group.

Other objects and advantages of the present invention will become apparent from the following description.

According to the present invention, firstly, the above objects and advantages of the present invention are attained by a photosensitive composition (may be referred to as "composition A" hereinafter) for forming a light transmitting material, comprising a silane compound or hydrolysis/dehydration condensation reaction product thereof, a photoinitiator and water, wherein the silane compound is represented by the following formula (1):

$$R^1SiX^1_3 \qquad (1)$$

wherein $R^1$ is an organic group having a polymerizable carbon-carbon double bond, and $X^1$ is a hydrolyzable group or atom, with the proviso that at least 40% of the total number of hydrogen atoms of the organic group $R^1$ are substituted by at least one substituent atom selected from the group consisting of deuterium, fluorine, chlorine and bromine.

According to the present invention, secondly, the above objects and advantages of the present invention are attained by a photosensitive composition (may be referred to as "composition B" hereinafter) for forming a light transmitting material, comprising:

(A) a metal compound represented by the following formula (2) or a hydrolysis/dehydration condensation reaction product thereof:

$$M^1X^2_4 \qquad (2)$$

wherein $M^1$ is Si, Al, Zr, Ge or Ti, and $X^2$ is a hydrolyzable group or atom;

(B) acrylic acid, methacrylic acid or acid ester thereof represented by the following formula (3):

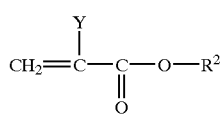

(3)

wherein $R^2$ is a hydrogen atom, alkyl group or ketoalkyl group, and Y is a hydrogen atom or methyl group, with the proviso that at least 40% of the total number of hydrogen atoms in the formula (3) are substituted by at least one substituent atom selected from the group consisting of deuterium, fluorine, chlorine and bromine;

(C) a photoinitiator; and (D) water.

According to the present invention, thirdly, the above objects and advantages of the present invention are attained by a photosensitive composition (may be referred to as "composition C" hereinafter) for forming a light transmitting material, comprising:

(A') a silane compound represented by the following formula (4) or a hydrolysis/dehydration condensation reaction product thereof:

$$R^3SiX^3_3 \qquad (4)$$

wherein $R^3$ is an organic group having a polymerizable carbon-carbon double bond, and $X^3$ is a hydrolyzable group or atom, with the proviso that some of the hydrogen atoms of the organic group $R^3$ may be substituted by at least one substituent atom selected from the group consisting of deuterium, fluorine, chlorine and bromine;

(B') a metal compound represented by the following formula (5) or a hydrolysis/dehydration condensation reaction product thereof:

$$M^2X^4_4 \qquad (5)$$

wherein $M^2$ is Si, Al, Zr, Ge or Ti, and $X^4$ is a hydrolyzable group or atom;

(C') acrylic acid, methacrylic acid or acid ester thereof represented by the following formula (6):

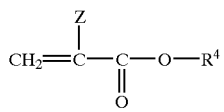

(6)

wherein $R^4$ is a hydrogen atom, alkyl group or ketoalkyl group, and Z is a hydrogen atom or methyl group, with the proviso that some of the hydrogen atoms in the formula (6) may be substituted by at least one substituent atom selected from the group consisting of deuterium, fluorine, chlorine and bromine;

(D') a photoinitiator; and (E') water, wherein the component (A') and the component (C') are used such that the above substituent atom(s) account(s) for at least 40% of the total of the hydrogen atoms of the organic group $R^3$ in the formula (4) and the hydrogen atoms in the formula (6).

According to the present invention, in the fourth place, the above objects and advantages of the present invention are attained by an optical waveguide element formed from the above composition A, B or C of the present invention.

According to the present invention, in the fifth place, the above objects and advantages of the present invention and attained by a process for producing an optical waveguide element comprising the steps of applying the photosensitive composition for forming a light transmitting material of the present invention to the surface of a substrate at least the surface layer of which has a low refractive index to form a film, exposing the film to ultraviolet radiation through a photomask placed upon the film, dissolving an unexposed film portion in a solvent to remove the portion according to circumstances, and thermally curing the film to form a core.

THE PREFERRED EMBODIMENTS OF THE INVENTION

The present invention will be described in detail hereinunder.

The silane compound represented by the above formula (1) in the composition A will be described. In the above formula (1). $R^1$ is an organic group having a polymerizable carbon-carbon double bond and $X^1$ is a hydrolyzable group or atom. Examples of $X^1$ include an alkoxyl group, alkenyloxy group and halogen atom. The organic group $R^1$ may be linear, branched or cyclic. It is preferably an organic group having a carbon-carbon double bond and 1 to 10 carbon atoms. The organic group $R^1$ is preferably an alkenyl group. This organic group is photosensitive.

The organic group is preferably an alkyl group or aryl group modified by vinyl group, vinyloxy group, allyl group, allyloxy group, acryl group, acryloxy group, methacryl group or methacryloxy group. Examples of the above modified alkyl group and aryl group include vinylalkyl groups such as vinylmethyl group and vinylethyl group; vinyloxyalkyl groups such as vinyloxymethyl group and vinyloxyethyl group; vinyl group, alkenyl group such as allyl group, acryl group and methacryl group; vinylaryl groups such as vinylphenyl group and vinyltolyl group; vinyloxyaryl groups such as vinyloxyphenyl group and vinyloxytolyl group; allylalkyl groups such as allylmethyl group and allylethyl group; allyloxyalkyl groups such as allyloxymethyl group and allyloxyethyl group; allylaryl groups such as allylphenyl group and allyltolyl group; allyloxyaryl groups such as allyloxyphenyl group and allyloxytolyl group; allylamino group; acrylalkyl groups such as acrylmethyl group and acrylethyl group; acryloxyalkyl groups such as acryloxymethyl group and acryloxyethyl group; methacrylalkyl groups such as methacrylmethyl group and methacrylethyl group; methacryloxyalkyl groups such as methacryloxymethyl group and methacryloxyethyl group; acrylaryl groups such as acrylphenyl group and acryltolyl group; acryloxyaryl groups such as acryloxyphenyl group and acryloxytolyl group; methacrylaryl groups such as methacrylphenyl group and methacryltolyl group; methacryloxyaryl groups such as methacryloxyphenyl group and methacryloxytolyl group; bicycloheptenyl group and (acryloxymethyl) phenethyl group. Out of these, methacryloxyalkyl groups are particularly preferred.

The alkoxyl group and alkenyloxy group as the hydrolyzable group represented by $X^1$ in the above formula (1) may be linear or branched and preferably have 1 to 4 carbon atoms. Examples of the halogen atom as the hydrolyzable atom represented by $X^1$ include fluorine, chlorine and bromine. Chlorine and fluorine are preferred.

Examples of the silane compound represented by the above formula (1) include 3-methacryloxyalkyl trialkoxysilane, 3-methacryloxyalkyl trichlorosilane, vinyltrimethoxysilane, vinyltriethoxysilane, 3-acryloxypropyltrimethoxysilane, 3-acryloxypropyltrichlorosilane, 3-(N-allylamino) propyltrimethoxysilane, allylaminotrimethoxysilane, (2-cyclohexenyl-2-ethyl)trialkoxysilane, allyltrialkoxysilane, 5-(bicycloheptenyl)trialkoxysilane, (acryloxymethyl)phenethyltrialkoxysilane, 1,1-bis (trialkoxysilylmethyl)ethylene, bis(triethoxysilyl)ethylene, bis(triethoxysilyl)-1,7-octanediene, butenyltriethoxysilane, 1-chloro-2-methylallyltrichlorosilane, 2-(chloromethyl) allyltrichlorosilane, [2-(3-cyclohexenyl)ethyl] trichlorosilane, 3-cyclohexenyltrichlorosilane, (4-cyclooctenyl)trichlorosilane, (3-cyclopentadienylpropyl) triethoxysilane, 5-hexenyltrialkoxysilane, O-(methacryloxyethyl)-N-(triethoxysilylpropyl)urethane, (2-methyl-propenyl)trimethylsilane, 1,7-octadienyltriethoxysilane, 7-octenyltrialkoxysilane, (2,4-pentadienyl)trialkoxysilane, styrylethyltrimethoxysilane and vinyltriisopropenoxysilane. Out of these, methacryloxyalkyltrialkoxysilane is particularly preferred.

In the composition A of the present invention, the silane compound represented by the above formula (1) is such that at least 40% of the total number of the hydrogen atoms of the organic group $R^1$ in the formula (1) are substituted by at least one substituent atom selected from the group consisting of deuterium (hydrogen isotope having a mass number of 2 or 3, may be abbreviated as D hereinafter), fluorine (F), chlorine (Cl) and bromine (Br). Preferably at least 60%, more preferably at least 80%, the particularly preferably 100% of the total number of the hydrogen atoms are substituted by the above substituent atom. Out of the above substituent atoms, deuterium is particularly preferred.

Since a small amount of an alkoxyl group or alkenyloxy group may remain in the film when $X^1$ in the above formula (1) is an alkoxyl group or alkenyloxy group, $X^1$ is preferably an alkoxyl group or alkenyloxy group substituted by deuterium.

The silane compound represented by the above formula (1) (may be referred to as "component (1)" hereinafter) is, for example, deuterated (3-methacryloxypropyltrimethoxysilane-d11) represented by the following formula (7), deuterated (3-methacryloxypropyltriethoxysilane-d26) represented by the following formula (8), deuterated (3-methacryloxyethyltrimethoxysilane-d18) represented by the following formula (9), deuterated (3-methacryloxypropyltrimethoxysilane-d5) represented by the following formula (10), deuterated and fluorinated (3-methacryloxyethyltriethoxysilane-d20) represented by the following formula (11), deuterated allyltrimethoxysilane-d13 represented by the following formula (12), deuterated vinyltrimethoxysilane-d11 represented by the following formula (13) or fluorinated alkyltrialkoxysilane represented by the following formula (14).

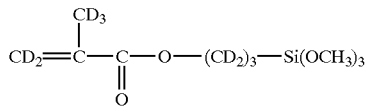

(7)

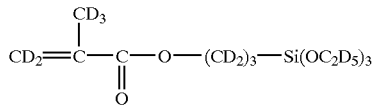

(8)

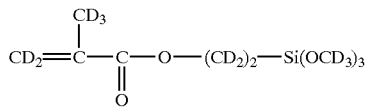

(9)

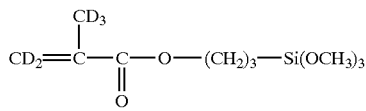

(10)

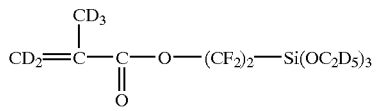

(11)

 (12)

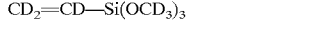 (13)

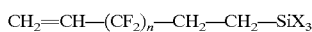 (14)

(in the formula (14), n=2 to 15, and X is an alkoxy group such as methoxy group or ethoxy group, with the proviso that the hydrogen atom of the alkoxy group may be substituted by a deuterium atom.)

The composition A of the present invention contains the above compound or hydrolysis/dehydration condensation reaction product thereof. When the degree of condensation of the condensation reaction product of this compound is too high, precipitation easily occurs. The degree of condensation is preferably 500 or less. The composition A contains a photointiator and water and optionally a solvent and a hydrolytic catalyst in addition to the compound of the formula (1) or hydrolysis/dehydration condensation reaction product thereof.

Water is required to complete the hydrolysis/dehydration condensation reaction of the above compound or hydrolysis/dehydration condensation reaction product thereof. Ordinary water ($H_2O$) may be used but it may remain in the obtained light transmitting material in a trace amount. In this case, a wavelength range absorbed by the OH group oscillation may overlap with communication wavelength ranges, thereby preventing light transmission. Therefore, heavy water ($D_2O$) is preferably used. Water is preferably added in a stoichiometric amount required for hydrolysis or more. When the amount of water is smaller than the stoichiometric amount, unreacted alkoxysilane remains at the time of a heat treatment for gelation. The amount of water is generally 0.8 to 30 times the required stoichiometric amount including water of an aqueous catalyst solution and the molar ratio of water to the component (1) is preferably 1:1 to 20:1, more preferably 2:1 to 10:1.

The solvent is preferably an alcohol. The alcohol is preferably a lower alcohol having 1 to 4 carbon atoms, particularly preferably methanol or ethanol having a low boiling point. The reason for this is that the alcohol can be removed rapidly from the solution by a heat treatment at a relatively low temperature after hydrolysis. The molar ratio of the alcohol to the component (1) is preferably 0.3:1 to 5:1, more preferably 0.5:1 to 1.5:1. To obtain a high light transmission at communication wavelength ranges, an alcohol having a deuterium atom substituted for a hydrogen atom is preferably used. Since the alcohol may be formed by the above hydrolytic reaction, it is not necessarily an essential component.

The catalyst is preferably an acid catalyst. The acid catalyst is preferably used in the form of an aqueous solution of at least one acid catalyst selected from formic acid, acetic acid, propionic acid, oxalic acid, hydrochloric acid, nitric acid and sulfuric acid. In this case, to obtain a high light transmission at communication wavelength ranges, an acid containing a deuterium atom substituted for a hydrogen atom is more preferably used. The amount of the acid catalyst differs according to the type of the acid and the strength of protonic acid (weak acid or strong acid). When the amount is too small, the proceeding of a hydrolysis/dehydration condensation reaction slows down and when the amount is too large, a condensation reaction proceeds too far, whereby the molecular weight becomes too large and the gelation of a precipitate and a coating solution readily occurs disadvantageously. Therefore, the amount of the acid catalyst added is preferably 0.01 to 10 mmol, more preferably 0.05 to 7 mmol based on 1 mol of the component (1) when hydrochloric acid is used as the acid catalyst.

The photoinitiator promotes photopolymerization when the organic group having a polymerizable carbon-carbon double bond contained in the composition A is exposed to light. Examples of the photoinitiator include 1-hydroxycyclohexyl-1-phenylketone (Irgacure 184 of CIBA Co., Ltd.), 2-hydroxy-2-methyl-1-phenylpropan-1-one (Darocure 1173 of Merk Co., Ltd.), 1-(4-isopropylphenyl)-2-hydroxy-2-methylpropan-1-one (Darocure 1116 of Merk Co., Ltd.) and 2,2-dimethoxy-2-phenylacetophenone (Irganocure 651 of CIBA Co., Ltd.). The amount of the photoinitiator is 0.001 to 0.2 mol based on 1 mol of the component (1) or 0.1 to 20 wt % based on the composition A.

Various additives may be contained in the composition A. Among the additives are a film thickness increasing agent, thickener, leveling agent and flow control agent, as exemplified by silicones such as dimethylpolysiloxane and glycols such as polyethylene glycol. The additives are also preferably those whose hydrogen atom is substituted by an atom selected from the group consisting of deuterium, fluorine, chlorine and bromine.

A description is subsequently given of the composition B. In the formula (2), $M^1$ is Si, Al, Zr, Ge or Ti, and $X^2$ is a hydrolyzable group or atom. $X^2$ is, for example, an alkoxyl group, alkenyloxy group or halogen atom. The alkoxyl group and alkenyloxy group as the hydrolyzable group $X^2$ may be linear or branched and preferably have 1 to 4 carbon atoms. The halogen atom as the hydrolyzable atom $X^2$ is, for example, fluorine, chlorine or bromine, out of which chlorine and fluorine are preferred. The alkoxyl group and alkenyloxy group represented by $X^2$ are preferably an alkoxyl group and alkenyloxy group substituted by deuterium, respectively. Examples of the metal compound (maybe referred to as "component (2)" hereinafter) represented by the above formula (2) include tetramethoxysilane, tetraethoxysilane, tetrabutoxyaluminum, tetrapropoxyzirconium, tetrabutoxyzirconium, tetraisopropoxytitanium, tetrabutoxytitanium, tetrachlorosilane, tetrachloroaluminum, tetrachlorozirconium, tetrachlorotitanium, tetramethoxygermane, tetraethoxygermane and tetraisopropoxygermane. A different metal alkoxide such as di-s-butoxyaluminoxytriethoxysilane may also be used. Out of these, the metal compound having an alkoxyl group is preferably a compound at least 40% (preferably at least 60%, more preferably at least 80%, the most preferably 100%) of the total number of hydrogen atoms of the alkoxyl group of which are substituted by at least one elemental atom selected from the group consisting of deuterium, fluorine, chlorine and bromine. Examples of the compound are deuterated tetramethoxysilane represented by the following formula (15), deuterated tetraethoxysilane represented by the following formula (16), deuterated tetrabutoxyaluminum represented by the following formula (17), deuterated tetrapropoxyzirconium represented by the following formula (18), deuterated tetrabutoxyzirconium represented by the following formula (19), deuterated tetraisopropoxytitanium represented by the following formula (20), deuterated tetrabutoxytitanium represented by the following formula (21), deuterated tetramethoxygermane represented by the following formula (22) and deuterated tetraethoxygermane represented by the following formula (23).

$$Si(OCD_3)_4 \quad (15)$$

$$Si(OCD_2CD_3)_4 \quad (16)$$

$$Al(OCD_2CD_2CD_2CD_3)_4 \quad (17)$$

$$Zr(OCD_2CD_2CD_3)_4 \quad (18)$$

$$Zr(OCD_2CD_2CD_2CD_3)_4 \quad (19)$$

$$Ti(OCD(CD_3)_2)_4 \quad (20)$$

$$Ti(OCD_2CD_2CD_2CD_3)_4 \quad (21)$$

$$Ge(OCD_3)_4 \quad (22)$$

$$Ge(OCD_2CD_3)_4 \quad (23)$$

The metal compound (component (2)) represented by the formula (2) may be contained in the composition B as it is, or may be contained in the composition B as a hydrolysis/dehydration condensation reaction product. In the latter case, when the degree of condensation of the condensation reaction product is too high, precipitation occurs. Therefore, the degree of condensation is preferably 500 or less.

The photosensitive (meth)acrylic compound represented by the above formula (3) used in the composition B of the present invention will be described hereinbelow. The alkyl group represented by $R^2$ in the formula (3) is preferably an alkyl group having 1 to 20 carbon atoms and the ketoalkyl group represented by $R^2$ is, for example, —$CH_2(CO)CH_2$ (CO)CH₃. Examples of the (meth)acrylic compound represented by the formula (3) include methacrylic acid, acrylic acid, methyl methacrylate, ethyl methacrylate, propyl methacrylate, butyl methacrylate, methyl acrylate, ethyl acrylate, propyl acrylate, butyl acrylate and methacryloxyacetyl acetonate.

The acrylic acid, methacrylic acid or acid ester thereof represented by the formula (3) in the present invention (may be referred to as "component (3)" hereinafter) is such that at least 40%, preferably at least 60%, more preferably at least 80%, the most preferably 100% of the total number of hydrogen atoms in the formula (3) are substituted by at least one substituent atom selected from the group consisting of deuterium, fluorine, chlorine and bromine. Examples of the compound include deuterated and fluorinated methyl methacrylate represented by the following formula (24), deuterated and fluorinated ethyl methacrylate represented by the following formula (25), deuterated and fluorinated propylmethacrylate represented by the following formula (26), deuterated and fluorinated butyl methacrylate represented by the following formula (27), methyl pentafluoromethacrylate represented by the following formula (28) and deuterated butyl methacrylate represented by the following formula (29).

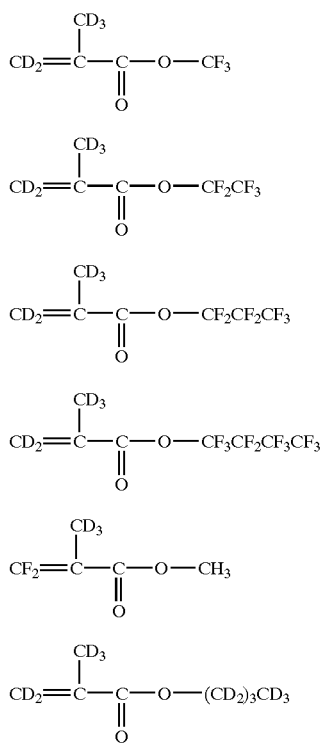

When M¹ of the compound represented by the above formula (2) is Al, Zr, Ge or Ti, the component (3) desirably stabilizes the component (2) to control the hydrolysis/condensation reaction of the compound of the formula (2). The component (3) is, for example, a carboxylic acid compound or chelating reagent. Examples of the compound include deuterated methacrylic acid and deuterated methacryloxydiacetylacetone compound. More specifically, they are compounds represented by the following formulas (30) to (33).

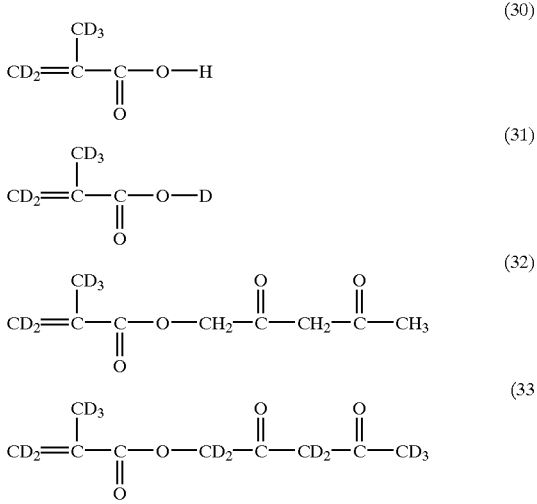

As for the composition B, the amounts of the component (2) and the component (3) will be described hereinbelow. The component (2) is a raw material which has excellent environmental resistance and heat resistance and gives an inorganic component for increasing refractive index whereas the component (3) gives flexibility to a film and photosensitivity to a material composition and has the function of reducing the refractive index of a film. Therefore, when the amount of the component (2) is too large, the flexibility of a film and the photosensitivity of a material composition are lost disadvantageously. When the amount of the component (3) is too large, environmental resistance and heat resistance are lost and the controllable range of refractive index is narrowed disadvantageously. The amount of the component (2) is in the range of preferably 25 to 75 mol %, more preferably 30 to 70 mol %, much more preferably 40 to 60 mol %. The amount of the component (3) is in the range of preferably 25 to 75 mol %, more preferably 30 to 70 mol %, much more preferably 40 to 60 mol %. The term "mol %" is based on the total number of mols of the component (2) and the component (3). The number of mols of the component (2) is based on the number of mols of the metal compound represented by the formula (2).

A description is subsequently given of each component of the composition C. The silane compound (may be referred to as "component (4)" hereinafter) represented by the above formula (4) will be first described. In the formula (4), R³ is an organic group having a polymerizable carbon-carbon double bond, and X³ is a hydrolyzable group or atom. Examples of the organic group and the hydrolyzable group or atom are the same as those enumerated for the above formula (1). In the formula (4), some or all of the hydrogen atoms of the above organic group may be substituted by a substituent atom selected from the group consisting of deuterium, fluorine, chlorine and bromine and does not always need to be substituted by the substituent atom unlike the formula (1). The component (4) gives flexibility to a film and photosensitivity to a material composition and has the function of reducing the refractive index of a film.

The metal compound represented by the formula (5) (may be referred to as "component (5)" hereinafter) may be identical to the metal compound represented by the above formula (2) which has been described for the composition B. This component has excellent environment resistance and heat resistance and is a raw material which gives an inorganic component for increasing refractive index.

A description is subsequently given of the acrylic acid, methacrylic acid or acid ester thereof represented by the formula (6) (maybe referred to as "component (6)" hereinafter). In the formula (6), $R^4$ is a hydrogen atom, alkyl group or ketoalkyl group, and Z is a hydrogen atom or methyl group. Examples of the alkyl group and ketoalkyl group are the same as those enumerated for the above formula (3). However, some or all of the hydrogen atoms in the formula (6) may be substituted by a substituent atom selected from the group consisting of deuterium, fluorine, chlorine and bromine and does not always need to be substituted by the substituent atom unlike the formula (3). This component (5) is a raw material which gives photosensitivity to a composition and a film.

In the composition C, the above component (4) and component (6) are used such that the above substituent atom(s) account(s) for at least 40% of the total number of the hydrogen atoms of the organic group $R^3$ in the formula (4) and the hydrogen atoms in the formula (6). A combination of the component (4) and the component (6) may be a combination of the component (4) and the component (6) all of which have a substituent atom or a combination of the component (4) and the component (6) either one of which has a substituent atom. When the component (4) has a substituent atom, it is preferred that at least 40% of the total number of hydrogen atoms of the organic group $R^3$ in the formula (4) is substituted by a substituent atom. When the component (6) has a substituent atom, it is preferred that at least 40% of the total number of hydrogen atoms in the formula (6) is substituted by a substituent atom. The above substituent atom is preferably deuterium.

When $R^4$ in the formula (6) is a substituent having a hydrogen atom and acetylacetone, this component is coordinately bonded to the component (5) and has a stabilization function. Therefore, it is preferred that the component (6) be existent in an amount of 1 mol or more based on 1 mol of the component (5) in this case. The amounts of the component (4), the component (5) and the component (6) are preferably in the ranges of 20 to 80 mol %, 10 to 40 mol % and 10 to 40 mol %, respectively.

The term mol % is based on the total number of mols of the component (4), the component (5) and the component (6), the number of mols of the component (4) is the number of mols of the silane compound represented by the formula (4) and the number of mols of the component (5) is the number of mols of the metal compound represented by the formula (5).

Either one or both of $X^3$ in the formula (4) and $X^4$ in the formula (5) are preferably an alkoxyl group or alkenyloxyl group substituted by deuterium.

The above description of the composition A is directly applied to water and a solvent which are contained in the above composition B and composition C, a photoinitiator and catalyst which are added as required, and additives which may be added. However, the amounts of water, solvent and catalyst are based on 1 mol of the component (2) in the case of the composition B and based on 1 mol of the total of the component (4) and the component (5) in the case of the composition C. The amount of the photoinitiator is based on 1 mol of the component (2) in the case of the composition B and based on 1 mol of the total of the component (4) and the component (5) in the case of the composition C.

A description is subsequently given of a process for forming an optical waveguide using the above photosensitive composition for forming a light transmitting material. The compositions A, B and C of the present invention have a polymerizable double bond. The refractive index of a composition obtained by polymerizing the above polymerizable double bond to increase the molecular weight is higher than the refractive index of a composition obtained by carrying out only dehydration polycondensation without polymerization. A core layer having a high refractive index can be formed on an exposed portion by applying a photosensitive sol-gel liquid composition containing a photoinitiator to the surface of a substrate at least the surface layer of which has a low refractive index to form a film, placing a photomask having a slit opening (ultraviolet light transmitting portion) upon the film, and exposing the film to ultraviolet radiation through the photomask. After exposure to ultraviolet radiation, a heat treatment is carried out to promote dehydration polycondensation so as to cure the film while the refractive index modulated by exposure to ultraviolet radiation is maintained. As for details of this process, please refer to New Developments in Integrated Optics Using the Sol-gel Process, P, Coudray et al, pp.286–303 and Sol-Gel and Polymer Photonic Devices, Mark P. Andrews, S. Iraj Najafi, Vol. CR68, SPIE (1997).

The exposed portion and the unexposed portion (unpolymerized portion) can be made different from each other in solubility in a solvent by polymerizing the double-bond portion exposed to ultraviolet radiation to increase the molecular weight. After exposure, the substrate is immersed in an acidic aqueous solution, alkaline aqueous solution or organic solvent to dissolve the unexposed portion, thereby making it possible to form a ridge type optical waveguide consisting of only the exposed portion (refer to 1st European Workshop on Hybrid Organic-Inorganic Materials, Nov. 8–10, 1993, New Journal of Chemistry, Vol. 18, pp.1125–1134, 1994).

An optical waveguide element or other light transmitting material is obtained by applying the above photosensitive composition (A, B or C) for forming a light transmitting material to a substrate to a wet thickness of 0.5 to 200 $\mu$m in a predetermined shape so as to form a film, exposing the film to ultraviolet radiation with a light intensity of 1 to 200 mW/cm$^2$ at an exposed position for 1 second to 2 minutes and curing the film by heating at 100 to 15° C. for 10 minutes to 5 hours. A photomask having a predetermined local light transmission distribution is placed upon the coating film before exposure to ultraviolet radiation, the surface of the film is treated with a solvent after exposure to ultraviolet radiation to dissolve and remove an unexposed portion, and the film is cured by heating at 100 to 150° C. for 10 minutes to 5 hours to obtain a light transmitting material having a predetermined shape.

The coating film of the photosensitive composition for forming a light transmitting material can be formed on the surface of the substrate by coating such as spin coating, dip coating, screen printing, gravure coating, flexographic printing or meniscus coating and has a uniform wet thickness, thereby making it possible to form a cured light transmitting material film having a uniform thickness.

The substrate used in the present invention may have any form such as a plate-like, bent plate-like or rod-like form. It is desired that the amount of warp of the surface of the substrate (length of thermal deformation in a direction perpendicular to the surface per unit length in the surface direction of the substrate) be small. When the amount of warp is beyond this range, the film may peel off from the substrate at the interface or crack in the step of molding a film. Therefore, the suitable material, size and shape of the substrate are preferably selected.

This substrate preferably has a linear expansion coefficient of $1.5 \times 10^{-5}$/° C. or less. When the linear expansion coefficient of this substrate is larger than $1.5 \times 10^{-5}/°$ C., in the case of a substrate made from a plastic having a high thermal expansion coefficient of 9 to $15 \times 10^{-5}/°$ C. such as polypropylene, the film may peel off from the substrate at the interface or crack in the step of molding an organopolysiloxane film. Ordinary inorganic glass has a linear expansion coefficient of $1.5 \times 10^{-5}/°$ C. or less. At least the surface of the substrate is preferably made from an oxide. When the surface in contact with the film of the substrate is not made from an oxide, adhesion strength lowers in the step of molding a film and the film may peel off from the substrate at the interface as the case may be. Preferred examples of the material of the substrate include oxide glasses such as silicate-based glass, boric acid-based glass and phosphoric acid-based glass, quartz, ceramics, metals, epoxy resins, glass fibers and reinforced polystyrene. Although a metal is not bonded to the film as it is, when the surface of the metal is treated with an oxidizing agent in advance, it can be used as the substrate. Out of these, float glass (linear expansion coefficient: $92 \times 10^{-7}/°$ C.) is preferred from the viewpoint of cost, and quartz glass (linear expansion coefficient: $8 \times 10^{-7}/°$ C.) and zero-expansion glass (linear expansion coefficient: $-3$ to $0.0 \times 10^{-7}/°$ C., trade name of Neocerum, Zerodua Glass) are the most preferred from the viewpoint of thermal expansion coefficient. To manufacture an integrated optical element, a silicon substrate (linear expansion coefficient: $41.5 \times 10^{-7}/°$ C.) may be used.

At least 40% of the total number of hydrogen atoms (excluding hydrogen atoms discharged to the outside of the light transmitting material by hydrolysis and dehydration reaction) contained in the organic group of the photosensitive composition for forming a light transmitting material of the present invention are substituted by at least one element selected from the group consisting of deuterium, fluorine, chlorine and bromine. The light absorption bands based on a C—D bond, C—F bond, C—Cl bond and C—Br bond are shifted toward a long wavelength side of that of a C—H bond and away from communication bands of 1.55 $\mu$m and 1.3 $\mu$m. A reduction in the transmission of communication bands of 1.55 $\mu$m and 1.3 $\mu$m of the light transmitting material caused by absorption based on the C—H bond can be prevented by the above substitution. Therefore, according to the present invention, a desired optical waveguide element or other optical element can be formed without impairing the transmission of communication bands of 1.55 $\mu$m and 1.3 $\mu$m. When the hydrogen atoms are substituted by fluorine, an increase in the optical loss of an optical element caused by moisture absorption can be prevented because the fluorine atom has a water-repelling effect.

A description is subsequently given of a process for fabricating a Brag diffraction grating in the optical waveguide of the present invention. The Bragg diffraction grating is formed from the photosensitive sol-gel liquid composition of the present invention as described above. As one of the methods of writing (adding) a Bragg diffraction grating to an optical waveguide by modulating refractive index and a ridge type optical waveguide by leaching after exposure, a phase mask is placed upon the optical waveguide and light from an excimer laser (wavelength: 249 nm (KrF) or 193 nm (ArF)) is irradiated onto the optical waveguide through the phase mask to induce the modulation of the Si—O—Si binding state of a metal oxide network, for example, a silica network of a film to make a difference in refractive index so as to write a diffraction grating (refer to M. P. Andrews, SPIE vol. 3282, pp. 50–54, 1998).

Alternatively, a double-beam interference exposure method (holographic method) may be used to write a Bragg diffraction grating. A He-Cd laser (325 nm, 421 nm) and Ar laser (351 nm) may be used as the light source used for this exposure. Exposure by an Ar ion laser (514.5 nm) may be made possible by using a sol-gel liquid composition having photosensitivity at a visible range and adding a visible light sensitizer. In order to produce an embedded or ridge type optical waveguide by light irradiation, a double-bond portion sufficient for holographic exposure for the formation of a diffraction grating must be left in the film by controlling irradiation energy.

The cycle of the formed grating (diffraction grating) can be controlled by the interference angle of coherent laser light to be interfered in the case of interference exposure. Meanwhile, the above cycle can be controlled by the cycle of grooves in a phase mask in the case of a phase mask method. By forming a grating cyclic structure in the core portion of an optical waveguide, a reflective optical filter which selectively reflects light having a specific wavelength can be formed. It is known that there is the following relationship among the reflection light wavelength, refractive index and refractive index (grating) cycle of the optical filter.

$$\lambda = 2 n_{eff} \cdot \Lambda$$

wherein neff is the effective refractive index in a mode for guiding an optical waveguide, and $\Lambda$ is the change cycle of refractive index. When the photosensitive composition for forming a light transmitting material of the present invention is used to selectively reflect light having a wavelength of 1.55 $\mu$m, $\Lambda$ is 0.5 $\mu$m because the refractive index is about 1.5. Thus, a narrow-band optical filter can be obtained. By changing the grating cycle A in an axial direction for guiding the light of the core portion of the optical waveguide, a wide-band optical filter having a chirped grating can be obtained.

EXAMPLES

The following examples are given to further illustrate the present invention.

Preparation of Deuterated Acetone Cyanhydrin (P1):

A 500 ml three-necked flask having a round bottom and equipped with a stirrer, separatory funnel and thermometer was prepared. A solution prepared by dissolving 50 g (95%, 0.97 mol) of powdery sodium cyanide in 120 ml of heavy water and 1.23 mols of deuterated acetone were placed in the flask. The flask was placed in iced bath and the solution was violently stirred. After the temperature of the solution was reduced to 15° C., 210 ml (0.85 mol) of 40% deuterated sulfuric acid was added dropwise over 3 hours while the temperature of the reaction solution was maintained at 10 to 20° C. After the end of addition of the acid, stirring was continued for 15 minutes and the flask was taken out and left to stand to precipitate a reaction product. A precipitated layer of deuterated acetone cyanhydrin was separated from a water phase by decantation. Sodium sulfate contained in the acetone cyanhydrin was separated and removed by filtration and the filtrate was cleaned with 5 ml of deuterated acetone three times. The obtained mixture of the filtrate and the acetone cleaning solution was added to heavy water and subjected to extraction with 25 ml of ether three times. The extract was mixed with the deuterated acetone cyanhydrin layer and dried with sodium sulfuric anhydride. The ether and acetone were separated from each other and removed by distillation and the residue was distilled under reduced pressure. The deuterated acetone cyanhydrin $((CD_3)_2C(OD)\cdot CN)$ was isolated at 78 to 82° C. and 15 mmHg. The yield was 64 g (yield rate: 77%).

Preparation of Deuterated Methacrylic Acid (P2):

1 mol of the deuterated acetone cyanhydrin (P1) and 1 mol of deuterated sulfuric acid were mixed together and stirred. Water was removed from the reaction mixture to obtain deuterated methacrylic acid ($CD_2=C(CD_3)COOD$) (P2).

Preparation of Deuterated Methyl Methacrylate (P3):

1 mol of the deuterated methacrylic acid (P2) and 1 mol of deuterated methanol ($CD_3OH$) were mixed together to obtain deuterated methyl methacrylate ($CD_2=C(CD_3)COO-CD_3$) (P3) through an esterification reaction.

Preparation of Deuterated and Fluorinated Methyl Methacrylate (PF1):

1 mol of the deuterated methacrylic acid (P2) and 1 mol of fluorinated methanol ($CF_3OH$) were mixed together to obtain deuterated and fluorinated methyl methacrylate ($CD_2-C(CD_3)COO-CF_3$) (P3) through an esterification reaction. All the eight hydrogen atoms contained in the methyl methacrylate were substituted by deuterium or fluorine.

Preparation of Deuterated Allyl Methacrylate (Allyl Methacrylate-d5) (P4):

1 mol of the deuterated and fluorinated methacrylic acid (P2) and 1 mol of allyl alcohol were mixed together to obtain deuterated allyl methacrylate ($CD_2-C(CD_3)COO-CH_2CH=CH_2$) (P4) through an esterification reaction.

Preparation of Deuterated Allyl Alcohol (Allyl Alcohol-d6) (P5):

Deuterated propylene (propylene-d6) was obtained from the dehydration reaction of deuterated 2-propanol (2-propanol-d8) in the presence of a catalyst. This was chlorinated under high temperature to convert it into allyl chloride which was then hydrolyzed using heavy water under an alkali condition to obtain deuterated allyl alcohol (allyl alcohol-d6, $CD_2=CDCD_2-OD$) (P5).

Preparation of Deuterated Allyl Methacrylate (Allyl Methacrylate-d10) (P6):

1 mol of the deuterated methacrylic acid (P2) and 1 mol of the deuterated allyl alcohol (P5) were mixed together to obtain deuterated allylmethacrylate (allyl methacrylate-d10, $CD_2-C(CD_3)COO-CD_2CD=CD_2$) (P6) through an esterification reaction.

Preparation of Deuterated Methacryloxypropyl Trichlorosilane (Methacryloxypropyl Trichlorosilane-d11) (P7):

1 mol of trichlorosilane and 1 mol of the deuterated allyl methacrylate (allyl methacrylate-d10) (P6) were added and reacted with each other to obtain deuterated methacryloxypropyl trichlorosilane (methacryloxypropyl trichlorosilane-d11, $CD_2=C(CD_3)COO(CD_2)_3-SiCl_3$) (P7).

Preparation of Deuterated Methacryloxypropyl Trimethoxysilane (Methacryloxypropyl Trimethoxysilane-d20) (P8):

1 mol of the deuterated methacryloxypropyl trichlorosilane (P7) and 3 mols of deuterated methanol (methanol-d4) were added and reacted with each other to obtain deuterated methacryloxypropyl trimethoxysilane (methacryloxypropyl trimethoxysilane-d20, $CD_2=C(CD_3)COO(CD_2)_3-Si(OCD_3)_3$) (P8). All the eleven hydrogen atoms contained in the methacryloxypropyl group were substituted by deuterium.

Preparation of Deuterated Tetraethoxysilane (TEOS-d20, (P9)):

1 mol of silicon tetrachloride and 4 mols of deuterated ethanol (ethanol-d6) were added and reacted with each other to obtain deuterated tetraethoxysilane ($Si(OC_2D_5)_4$) (P9).

Preparation of Deuterated Tetrapropoxyzirconium (Tetrapropoxyzirconium-d28) (P10):

1 mol of zirconium tetrachloride and 4 mols of deuterated 2-propanol (2-propanol-d8) were added and reacted with each other to obtain deuterated tetrapropoxyzirconium ($Zr(OC_3D_7)_4$) (P10).

Preparation of Deuterated Tetrabutoxyzirconium (Tetrabutoxyzirconium-d36) (P11):

1 mol of zirconium tetrachloride and 4 mols of deuterated butanol (butanol-d10) were added and reacted with each other to obtain deuterated tetrabutoxyzirconium ($Zr(OC_4D_9)_4$) (P11).

Preparation of Fluorinated Alkylsilane IP12):

2.54 g (0.01 mol) of 1,4-divinyloctafluorobutane [$(CF_2)_4(CH=CH_2)_2$)] and 1.64 g (0.01 mol) of triethoxysilane were added and stirred at room temperature for 30 minutes. A catalytic amount of chloroplatinic acid was added to the resulting mixture and stirred at room temperature for 24 hours. The residual catalyst was removed by centrifugal separation, and unreacted triethoxysilane and 1,4-divinyloctafluorobutane were distilled off under reduced pressure to obtain $CH_2=CH(CF_2)_4(CH_2)_2Si(OC_2H_5)_3$ (6-vinyl-3,3,4,4,5,5,6,6-octafluorohexyl triethoxysilane). Eight out of the 15 hydrogen atoms contained in the vinylhexyl group were substituted by fluorine.

Preparation of Composition (A1):

1 mol of the deuterated methacryloxypropyl trimethoxysilane (P8) and 0.75 mol (including 0.05 mol of deuterated hydrochloric acid) of a heavy water solution were mixed together and hydrolyzed for 2 hours. This hydrolysate was charged into a beaker and 2-hydroxy-2-methyl-1-phenylpropan-1-one (Darocure 1173 of Merk Co., Ltd.) was added as a photoinitiator to the beaker in an amount of 2 wt % based on the total weight to obtain a composition (A1).

Preparation of Composition (A2):

1 mol of the deuterated methacryloxypropyl trimethoxysilane (P8) and 0.75 mol (including 0.05 mol of deuterated hydrochloric acid) of a heavy water solution were mixed together and hydrolyzed for 2 hours. This hydrolysate was charged into a beaker and 2-hydroxy-2-methyl-1-phenylpropan-1-one (Darocure 1173 of Merk Co., Ltd.) was added as a photoinitiator to the beaker in an amount of 2 wt % based on the total weight to obtain a composition (A2).

Preparation of Composition (B1):

80 g of the deuterated tetraethoxysilane (P9), 10 g of polydimethylsiloxane ($H-(Si(CH_3)_2-O)_nOH$, Petrarch Systems, Inc. trade name: PS340, molecular weight: 1700) as a film thickness increasing agent, 20 ml of deuterated tetrahydrofuran ($C_4D_4O$), 30 ml of deuterated isopropanol (2-propanol-d8) and 16 g of a heavywater solution of deuterated hydrochloric acid (7 g of deuterated hydrochloric acid dissolved in heavy water) were charged into a beaker and stirred under ref lux at 80° C. for 30 minutes. 4.75 g of the deuterated and fluorinated methyl methacrylate (PF1) and 2 wt % based on the total weight of 2-hydroxy-2-methyl-1-phenylpropan-1-one (Darocure 1173 of Merk Co., Ltd.) as a photoinitiator were added to the beaker to obtain a composition (B1).

Preparation of Composition (B2):

A composition (B2) was obtained in the same manner as the preparation of the above composition (B1) except that the same amount of methylpentafluoromethacrylate (above formula (28)) was used in place of the deuterated and fluorinated methyl methacrylate (PF1).

Preparation of Composition (B3):

A composition (B3) was obtained in the same manner as the preparation of the above composition (B1) except that the same amount of the deuterated methyl methacrylate (P3) was used in place of the deuterated and fluorinated methyl methacrylate (PF1).

Preparation of Composition (B4)

A composition (B4) was obtained in the same manner as the preparation of the above composition (B1) except that the same amount of the deuterated allyl methacrylate (P4) was used in place of the deuterated and fluorinated methyl methacrylate (PF1).

Preparation of Composition (B5):

A composition (B5) was obtained in the same manner as the preparation of the above composition (B1) except that the same amounts of tetraethoxysilane, tetrahydrofuran, isopropanol, an aqueous solution of hydrochloric acid and methyl methacrylate were used in place of the deuterated tetraethoxysilane (P9), deuterated tetrahydrofuran ($C_4D_4O$), deuterated isopropanol (2-propanol-d8), heavywater solution of deuterated hydrochloric acid and deuterated and fluorinated methyl methacrylate (PF1), respectively.

Preparation of Composition (C1):

The deuterated methacryloxypropyl trimethoxysilane (P8) which was hydrolyzed with 0.75 molar equivalent of a heavy water solution (including 0.05 mol of deuterated hydrochloric acid) for 2 hours in advance and the deuterated tetrapropoxyzirconium (P10) which was stabilized by 1 molar equivalent of the deuteratedmethacrylic acid (P2) were added to a beaker in a P8/P10/P2 molar ratio of 10/4/4. Heavy water was added in an amount of 2 molar equivalents based on the deuteratedtetrapropoxyzirconium (P10) and stirred for 2 hours. 2-hydroxy-2-methyl-1-phenylpropan-1-one (Darocure 1173 of Merk Co., Ltd.) was added as a photoinitiator in an amount of 2 wt % based on the total weight to obtain a composition (C1).

Preparation of Composition (C2):

A composition (C2) was obtained in the same manner as the preparation of the above composition (C1) except that the deuterated tetrabutoxyzirconium (P11) was used in place of the deuterated tetrapropoxyzirconium (P10).

Preparation of Compositions D1 and D2 for Forming Optical Waveguide:

0.37 g of the raw material P12, 0.168 g of hydrochloric acid having a concentration of 0.1 mol/l, 0.46 g of diethoxysiloxane-s-butylaluminate, 1.0 g of tetraethoxysilane, 0.3 g of isopropanol and 0.4 g of water were added and reacted at room temperature for 24 hours (liquid composition D1). Darocure 1173 was added as a photoinitiator to the reaction solution in an amount of 3 wt % based on the total weight to obtain a liquid composition D2.

Example 1

Fabrication of Optical Waveguide (1):

A silicon (Si) substrate (2×2 cm) covered with a 3 $\mu$m thick $SiO_2$ layer (refractive index: 1.46) was ultrasonically cleaned in isopropanol for 20 minutes and further in pure water for 20 minutes. The composition (A1) was dropped on the substrate and spin coated to form a uniform coating film on the substrate. This film was dried by heating at 100° C. for 30 minutes. A photomask (2 cm×2 cm, a 2 cm long and 8 $\mu$m wide light transmitting slit formed at the center) was placed upon the film which was then exposed to 5 eV ultraviolet radiation (wavelength of 365 nm) from a distance of 30 cm for 1 minute. The intensity of ultraviolet radiation on the film plane was 10 mW/cm². The polymerizable carbon-carbon double bond of the methacryloxy group of methacryloxypropyl trimethoxysilane was cleaved in the exposed portion of the film to form methacryloxypropyl trimethoxysilane which is a polymer insoluble in isopropanol by this exposure. However, the above polymer was not formed in the unexposed portion which had solubility in isopropanol. After the end of exposure, the substrate was immersed in isopropanol to dissolve the unexposed portion. The substrate was dried at 120° C. for 2 hours to complete the dehydration condensation reaction of methacryloxypropyl trimethoxysilane, thereby obtaining a 8 $\mu$m×8 $\mu$m and 2 cm long ridge type optical waveguide (1) (refractive index of the core portion: 1.48) on the $SiO_2$ layer of the silicon substrate. The optical loss of the optical waveguide element was 0.42 dB/cm (light having a wavelength of 1.55 $\mu$m) or 0.02 dB/cm (light having a wavelength of 1.3 $\mu$m).

The optical loss of the optical waveguide element was measured as follows. Laser light having a wavelength of 1.55 $\mu$m (and 1.3 $\mu$m) was introduced into the core portion of the optical waveguide by a collimator lens through an optical fiber and transmitted light was detected by an optical power meter and an optical spectral analyzer.

Example 2

Fabrication of Optical Filter (1):

A quartz glass plate (linear expansion coefficient: 5.5× $10^{-7}$/° C., refractive index: 1.460 (light having a wavelength of 633 nm), size: 20 mm×20 mm×2.0 mm) was ultrasonically cleaned in isopropanol for 20 minutes and further in pure water for 20 minutes. The composition (B1) was dropped on this substrate and spin coated to form a uniform coating film on the substrate. This film was dried by heating at 60° C. for 30 minutes. The hydrolysis and polycondensation reaction of deuterated tetraethoxysilane contained in the film proceeded by this drying. The film was exposed to light from a He—Cd laser (wavelength: 325 nm) by a double-beam interference exposure method for 1 minute. The intensity of ultraviolet radiation of a portion exposed to an interference fringe on the film plane was 10 mW/cm². Thereafter, the film was heated at 120° C. for 1 hour. Thereby, an optical filter having a phase type (refractive index modulation type) grating with a cycle of 0.5 $\mu$m was obtained. It was confirmed that the film had an average refractive index of 1.480 (633 nm) and a thickness of 3.0 $\mu$m and a plane optical waveguide having a phase type (refractive index modulation type) grating was formed. The insertion loss was 0.82 dB/cm (1.55 $\mu$m) or 0.04 dB/cm (1.3 $\mu$m). It was assumed that the obtained film had such a structure that silica constituted a network and deuterated methyl methacrylate was existent in spaces of the network. Deuterated and fluorinated methyl methacrylate having a high degree of polymerization was formed in a portion (width of about 210 nm and intervals between highest light intensity portions of 420 nm) having a high light intensity of the interference fringe of the film whereas deuterated and fluorinated methyl methacrylate was not formed or deuterated and fluorinated methyl methacrylate having a low degree of polymerization was formed in a portion (width of about 210 nm) having a low light intensity of the interference fringe. Since the deuterated methyl methacrylate having a high degree of polymerization had a higher refractive index than a monomer thereof or the deuterated methyl methacrylate having a low degree of polymerization, it was considered that a core portion exposed to the interference fringe had a higher refractive index (difference in refractive index of about 0.0001) than a core portion unexposed to the interference fringe, thereby forming a phase type grating.

Example 3

Fabrication of Optical Waveguide (2):

A silicon substrate (1.0×20×20 mm) covered with a 3 $\mu$m thick $SiO_2$ layer (refractive index: 1.46) was ultrasonically cleaned in isopropanol for 20 minutes and further in pure water for 20 minutes. The composition (C1) was dropped on the substrate and spin coated to form a uniform coating film on the substrate. This film was dried by heating at 100° C. for 30 minutes. The same photomask (pitch: 8 μm) as used in Example 1 was placed upon the film which was then exposed to 5 eV ultraviolet radiation from a distance of 30 cm for about 1 minute. The polymerizable carbon-carbon double bonds of the methacryloxy groups of methacryloxypropyl trimethoxysilane and deuterated methacrylic acid were cleaved in the exposed portion of the film by this exposure, thereby forming methacryloxypropyl trimethoxysilane and methacrylic acid (non-soluble in isopropanol). However, these polymers were not formed in the unexposed portion which had solubility in isopropanol. After the end of exposure, the substrate was immersed in isopropanol to dissolve and remove the unexposed portion. The substrate was then dried at 120° C. for 2 hours to complete the dehydration condensation reaction of methacryloxypropyl trimethoxysilane so as to obtain a 8 μm×8 μm×20 mm ridge type optical waveguide (2) which was the same in size as in Example 1. The refractive index of the core was 1.501. When the optical loss of the optical waveguide was measured in the same manner as in Example 1, it was 0.43 dB/cm (light having a wavelength of 1.55 μm) or 0.03 dB/cm (light having a wavelength of 1.3 μm).

Example 4
Fabrication of Optical Filter (2):

A phase mask having a cyclic structure Λ of 1,055 nm was placed upon the ridge type optical waveguide (2) obtained in Example 3 such that its parallel engravings became perpendicular to the lengthwise direction of the waveguide and the optical waveguide was irradiated with excimer laser light having a wavelength of 193 nm so as to directly form a grating in the core portion of the optical waveguide in a direction perpendicular to the major axis direction of the core portion. It was considered that a grating was formed as polymer portions (methacryloxypropyl trimethoxysilane and methacrylic acid) exposed through a mask and at intervals of about 1 μm had a higher degree of polymerization and a higher refractive index than unexposed polymer portions.

Example 5
Fabrication of Optical Waveguide (3):

A ridge type optical waveguide (2) was obtained in the same manner as in Example 1 except that the composition (A2) was used in place of the composition (A1) in the fabrication of optical waveguide (1). The optical loss of the optical waveguide was 0.87 dB/cm (1.55 μm) or 0.04 dB/cm (1.3 μm).

Example 6
Fabrication of Optical Filter (3):

An optical filter (3) was obtained in the same manner as in Example 2 except that the composition (B2) was used in place of the composition (B1) in the fabrication of optical filter (1). It was confirmed that a plane optical waveguide having a phase type (refractive index modulation type) grating with a film refractive index of 1.475 (633 nm) and a film thickness of 3.3 μm was formed. The insertion loss was 0.89 dB/cm (1.55 μm) or 0.07 dB/cm (1.3 mp).

Example 7
Fabrication of Optical Filter (4):

An optical filter (4) was obtained in the same manner as in Example 2 except that the composition (B3) was used in place of the composition (B1) in the fabrication of optical filter (1). It was confirmed that a plane optical waveguide having a phase type (refractive index modulation type) grating with a film refractive index of 1.480 (633 nm) and a film thickness of 3.0 μm was formed. The insertion loss was 0.82 dB/cm (1.55 μm) or 0.05 dB/cm (1.3 mμ).

Example 8
Fabrication of Optical Filter (5):

An optical filter (5) was obtained in the same manner as in Example 2 except that the composition (B4) was used in place of the composition (B1) in the fabrication of optical filter (1). It was confirmed that a plane optical waveguide having a phase type (refractive index modulation type) grating with a film refractive index of 1.481 (633 nm) and a film thickness of 2.8 μm was formed. The insertion loss was 0.93 dB/cm (1.55 μm) or 0.08 dB/cm (1.3 mμ).

Example 9
Fabrication of Optical Waveguide (4):

A silicon substrate (1.0×20×20 mm) covered with a 3 μm thick $SiO_2$ layer (refractive index: 1.46) was ultrasonically cleaned in isopropanol for 20 minutes and further in pure water for 20 minutes. The composition (B5) was dropped on the substrate and spin coated to form a uniform coating film on the substrate. This film was dried by heating at 100° C. for 30 minutes. A photomask (pitch: 8 μm) was placed upon the film which was then exposed to 5 eV ultraviolet radiation from a distance of 30 cm. After the end of exposure, the substrate was immersed in isopropanol to dissolve an unexposed portion. Then, the substrate was dried at 120° C. for 2 hours to obtain a ridge type optical waveguide (4).

Example 10
Fabrication of Optical Waveguide (5):

An optical waveguide (5) was produced in the same manner as in Example 3 except that the composition (C2) was used in place of the composition (C1) in the fabrication of the optical waveguide (2) of Example 3.

Example 11
Fabrication of Optical Waveguide With Diffraction Grating:

A silicon substrate covered with a 2 μm thick $SiO_2$ layer (refractive index: 1.46) was spin coated with the liquid composition D2 and dried at 60° C. for 30 minutes. Then, the substrate was further spin coated with the liquid composition D1 and dried at 60° C. for 30 minutes. A photomask having a 6 μm wide and 2 cm long slit opening was placed upon the formed films of the substrate and exposed to light from a fluorescent lamp for 30 seconds. The layer of the liquid composition D2 was exposed to ultraviolet radiation passing from the opening of the photomask through the layer of the liquid composition D1. The polymerization of fluorinated alkylsilane containing a vinyl group (P12) proceeded in the exposed portion of the D2 layer but rarely proceeded in the unexposed portion of the D2 layer. As a result, the exposed portion of the D2 layer corresponding to the core of an optical waveguide had a refractive index of 1.488 and the unexposed portion of the D2 layer corresponding to the clad (side portion) of the optical waveguide had a refractive index of 1.485. An embedded type optical waveguide having a 8 μm thick core layer (n=1.488) and a 4 μm thick overclad layer (D1 layer) (n=1.485) was thus produced.

A Bragg diffraction grating was formed on the thus produced embedded type optical waveguide by a double-beam interference exposure method using a He—Cd laser. The optical waveguide was exposed to light having a wavelength of 325 nm at θ of 21.8° (θ: inclination from the normal of the plane of the optical waveguide) and heated at 150° C. for 30 minutes. The polymerization of the fluorinated alkylsilane containing a vinyl group further proceeded in the core layer portion exposed by the interference exposure method but did not proceed further in the unexposed core layer portion. As a result, a high-refractive index portion where the above polymerization proceeded and a low-refractive index portion where polymerization did not proceed were formed in the core layer of the optical waveguide. Thereby, a Bragg diffraction grating was formed in the core layer of the optical waveguide. When the loss peak caused by Bragg reflection of the obtained optical waveguide having a Bragg diffraction grating was measured by a spectral analyzer, it was 1,300 nm. When the transmission loss was evaluated by guiding light having a wavelength of 1,550 nm, it was 0.4 dB/cm.

Comparative Example 1

An optical waveguide was manufactured in the same manner as in Example 1 except that a composition prepared by using methacryloxypropyl trimethoxysilane was used in place of the deuterated methacryloxypropyl trimethoxysilane (P8) in the composition (A1). The optical loss of the optical waveguide was 3.5 dB/cm (1.55 μm) or 0.55 dB/cm (1.30 μm).

Comparative Example 2
Fabrication of Optical Filter (5):

An optical filter (5) was manufactured in the same manner as in Example 2 except that the composition (B5) was used in place of the composition (B1) in the fabrication of optical filter (1). It was confirmed that a plane optical waveguide having a phase type (refractive index modulation type) grating with a film refractive index of 1.480 (633 nm) and a film thickness of 3.1 μm was formed. The insertion loss was 9.50 dB/cm (1.55 μm) or 5.08/cm (1.3 μm).

The present invention can provide a photosensitive composition for forming an optical part which has high transmission at wavelength ranges used for communication and excellent characteristic properties such as heat resistance, water resistance and chemical resistance, and makes it possible to form a grating and incorporate it in a mounting module with ease.

Since at least 40% of the total number of hydrogen atoms of the silicon compound having a polymerizable substituent of the present invention are substituted by at least one elemental atom selected from the group consisting of deuterium, fluorine, chlorine and bromine, it is not necessary to add methacryloxypropylmethyl dichlorosilane having a high content of an organic component to reduce the amount of a C—H group or to add heptadecafluorodecyl methacrylate having a high content of an organic component to reduce the amount of a C—H group and exhibit photosensitivity. As a result, there can be provided a material composition which enables the control of the proportions of an organic component and an inorganic component in a wide range. The polymerizable substituent of the silicon compound having a polymerizable substituent of the present invention can be used as a material for fine light processing as it has excellent optical processability.

What is claimed is:

1. A photosensitive composition for forming a light transmitting material, comprising a silane compound or a hydrolysis/dehydration condensation reaction product thereof, a photoinitiator and water, wherein
the silane compound is represented by the following formula (1):

$$R^1SiX^1_3 \qquad (1)$$

wherein $R^1$ is an organic group having a polymerizable carbon-carbon double bond, and $X^1$ is a hydrolyzable group or atom, with the proviso that at least 40% of the total number of hydrogen atoms of the organic group $R^1$ are substituted by at least one substituent atom selected from the group consisting of deuterium, fluorine, chlorine and bromine.

2. The photosensitive composition of claim 1, wherein the organic group is an alkenyl group.

3. The photosensitive composition of claim 1, wherein the organic group is a vinyl group, allyl group, acryl group or methacryl group.

4. The photosensitive composition of claim 1, wherein the organic group is an alkyl group or aryl group modified by a vinyl group, vinyloxy group, allyl group, allyloxy group, acryl group, acryloxy group, methacryl group or methacryloxy group.

5. The photosensitive composition of claim 4, wherein the organic group is a methacryloxyalkyl group.

6. The photosensitive composition of claim 1, wherein said at least one substituent atom is deuterium.

7. The photosensitive composition of claim 1, wherein said $X^1$ is an alkoxyl group substituted by deuterium or an alkenyloxy group substituted by deuterium.

8. A photosensitive composition for forming a light transmitting material, comprising:
(A) a metal compound represented by the following formula (2) or a hydrolysis/dehydration condensation reaction product thereof:

$$M^1X^2_4 \qquad (2)$$

wherein $M^1$ is Si, Al, Zr, Ge or Ti, and $X^2$ is a hydrolyzable group or atom;
(B) acrylic acid, methacrylic acid or acid ester thereof represented by the following formula (3):

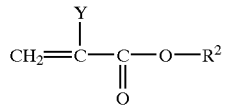

wherein $R^2$ is a hydrogen atom, alkyl group or ketoalkyl group, and Y is a hydrogen atom or methyl group, with the proviso that at least 40% of the total number of hydrogen atoms in the formula (3) are substituted by at least one substituent atom selected from the group consisting of deuterium, fluorine, chlorine and bromine;
(C) a photoinitiator; and
(D) water.

9. The photosensitive composition of claim 8 which comprises the component (A) as a metal compound represented by the above formula (2) in an amount of 25 to 75 mol % and the component (B) in an amount of 75 to 25 mol % based on the total number of mols of the component (A) as the metal compound represented by the above formula (2) and the component (B).

10. The photosensitive composition of claim 8, wherein said at least one substituent atom in the above formula (3) is deuterium.

11. The photosensitive composition of claim 8, wherein said $X^2$ in the above formula (2) is an alkoxyl group or alkenyloxy group substituted by deuterium.

12. A photosensitive composition for forming a light transmitting material, comprising:
(A') a silane compound represented by the following formula (4) or a hydrolysis/dehydration condensation reaction product thereof:

$$R^3SiX^3_3 \quad (4)$$

wherein $R^3$ is an organic group having a polymerizable carbon-carbon double bond, and $X^3$ is a hydrolyzable group or atom, with the proviso that some or all of the hydrogen atoms of the organic group $R^3$ may be substituted by at least one substituent atom selected from the group consisting of deuterium, fluorine, chlorine and bromine;

(B') a metal compound represented by the following formula (5) or a hydrolysis/dehydration condensation reaction product thereof:

$$M^2X^4_4 \quad (5)$$

wherein $M^2$ is Si, Al, Zr, Ge or Ti, and $X^4$ is a hydrolyzable group or atom;

(C') acrylic acid, methacrylic acid or acid ester thereof represented by the following formula (6):

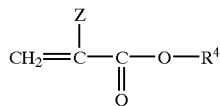

(6)

wherein $R^4$ is a hydrogen atom, alkyl group or ketoalkyl group, and Z is a hydrogen atom or methyl group, with the proviso that some or all of the hydrogen atoms in the formula (6) may be substituted by at least one substituent atom selected from the group consisting of deuterium, fluorine, chlorine and bromine;

(D') a photoinitiator; and (E') water, wherein the component (A') and the component (C') are used such that the above substituent atom(s) account(s) for at least 40% of the total of the hydrogen atoms of the organic group $R^3$ in the formula (4) and the hydrogen atoms in the formula (6).

13. The photosensitive composition of claim 12 which comprises the component (A') as a silane compound represented by the above formula (4) in an amount of 20 to 80 mol %, the component (B') as a metal compound represented by the above formula (5) in an amount of 10 to 40 mol % and the component (C') in an amount of 10 to 40 molt based on the total of the number of mols of the component (A') as the silane compound represented by the above formula (4), the number of mols of the component (B') as the metal compound represented by the above formula (5) and the number of mols of the component (C').

14. The photosensitive composition of claim 12, wherein the substituent atom is deuterium.

15. The photosensitive composition for forming a light transmitting material of claim 12, wherein either one or both of $X^3$ in the above formula (4) and $X^4$ in the above formula (5) is or are an alkoxyl group substituted by deuterium or an alkenyloxy group substituted by deuterium.

16. An optical waveguide element made from the photosensitive composition for forming a light transmitting material of any one of claims 1, 8 or 12.

17. An optical waveguide element having a grating made from the photosensitive composition for forming a light transmitting material of any one of claims 1, 8 or 12.

18. A process for producing an optical waveguide element, comprising the steps of:

applying the photosensitive composition for forming a light transmitting material of any one of claims 1, 8 or 12 to the surface of a substrates at least the surface layer of which has a low refractive index to form a film, exposing the film to ultraviolet radiation through a photomask placed upon the film, dissolving an unexposed film portion in a solvent to remove the portion, and thermally curing the film to form a core.

19. A process for producing an optical waveguide element having a diffraction grating, comprising the steps of:

exposing the optical waveguide element of claim 18 to ultraviolet radiation by an interference exposure method or phase mask method and thermally curing the element to form a diffraction grating in the core layer of the optical waveguide.

20. A process for producing an optical waveguide element, comprising the steps of:

applying the photosensitive composition for forming a light transmitting material of any one of claims 1, 8 or 12 to the surface of a substrate at least the surface layer of which has a low refractive index to form a film, exposing the film to ultraviolet radiation through a photomask placed upon the film and thermally curing the film to form a core.

21. A process for producing an optical waveguide element having a diffraction grating, comprising the steps of:

exposing the optical waveguide element of claim 20 to ultraviolet radiation by an interference exposure method or phase mask method and thermally curing the element to form a diffraction grating in the core layer of the optical waveguide.

22. A process for producing a plane optical waveguide element having a diffraction grating, comprising the steps of:

applying the photosensitive composition for forming a light transmitting material of any one of claims 1, 8 or 12 to the surface of a substrate at least the surface layer of which has a low refractive index to form a film, exposing the film to ultraviolet radiation by an interference exposure method or phase mask method and thermally curing the film.

* * * * *